(12) United States Patent
Gu et al.

(10) Patent No.: US 10,932,755 B2
(45) Date of Patent: Mar. 2, 2021

(54) ULTRASONIC PROBE

(71) Applicant: SAMSUNG MEDISON CO., LTD., Hongcheon-gun (KR)

(72) Inventors: Jin Ho Gu, Yongin-si (KR); Sung Do Kwon, Yongin-si (KR); Seong Jin Kim, Hwaseong-si (KR); Joong Hyun Park, Seoul (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 379 days.

(21) Appl. No.: 15/868,637

(22) Filed: Jan. 11, 2018

(65) Prior Publication Data

US 2018/0235575 A1 Aug. 23, 2018

(30) Foreign Application Priority Data

Feb. 21, 2017 (KR) ........................ 10-2017-0022835

(51) Int. Cl.
*H01L 41/04* (2006.01)
*A61B 8/14* (2006.01)
(Continued)

(52) U.S. Cl.
CPC .......... *A61B 8/4494* (2013.01); *A61B 8/4444* (2013.01); *B06B 1/0622* (2013.01);
(Continued)

(58) Field of Classification Search
CPC ... A61B 8/4494; A61B 8/4444; A61B 8/4483; B06B 1/0622; G01S 7/521; G01S 15/8915
(Continued)

(56) References Cited

U.S. PATENT DOCUMENTS 5,311,095 A 5/1994 Smith et al.
5,834,880 A 11/1998 Venkataramani et al.
(Continued)

FOREIGN PATENT DOCUMENTS

JP 2012-182758 A 9/2012
KR 10-2010-0091466 A 8/2010

OTHER PUBLICATIONS

Extended European Search Report dated Jul. 13, 2018 issued in European Patent Application No. 18157636.4.
(Continued)

*Primary Examiner* — Thomas M Dougherty
(74) *Attorney, Agent, or Firm* — Morgan, Lewis & Bockius LLP

(57) ABSTRACT

Disclosed herein is a multi-row ultrasonic probe of which a manufacturing failure rate can be decreased. The ultrasonic probe includes a piezoelectric layer configured to generate ultrasonic waves, a sound layer provided on a rear side of the piezoelectric layer, a flexible printed circuit board provided on a rear side of the sound layer, and a sound absorption layer configured to absorb the ultrasonic waves generated by the piezoelectric layer and propagating toward a rear surface of the ultrasonic probe, the sound absorption layer being provided on a rear surface of the flexible printed circuit board. The piezoelectric layer includes a kerf configured to divide the piezoelectric layer in a direction of elevation. The sound layer includes a funnel extending in a direction extending from a front side of the sound layer to the rear side of the sound layer to divide the sound layer.

13 Claims, 9 Drawing Sheets

(51) Int. Cl.
  *A61B 8/00*    (2006.01)
  *B06B 1/06*    (2006.01)
  *G01S 15/89*   (2006.01)
  *G01S 7/521*   (2006.01)

(52) U.S. Cl.
  CPC ............ *A61B 8/4483* (2013.01); *G01S 7/521* (2013.01); *G01S 15/8915* (2013.01)

(58) Field of Classification Search
  USPC ........................................................ 310/334
  See application file for complete search history.

(56) References Cited

U.S. PATENT DOCUMENTS

| | | | |
|---|---|---|---|
| 5,882,309 A | 3/1999 | Chiao et al. | |
| 8,410,666 B2* | 4/2013 | Shikata | H01L 41/27 |
| | | | 310/334 |
| 9,668,715 B2* | 6/2017 | Gu | B06B 1/0622 |
| 2003/0073906 A1 | 4/2003 | Flesch et al. | |
| 2008/0315724 A1 | 12/2008 | Kunkel, III | |
| 2011/0295124 A1 | 12/2011 | Shikata et al. | |
| 2015/0045671 A1 | 2/2015 | Ozawa | |
| 2015/0051493 A1 | 2/2015 | Gu et al. | |
| 2015/0157292 A1 | 6/2015 | Gu et al. | |

OTHER PUBLICATIONS

European Office Action dated Jul. 13, 2020 issued in European Patent Application No. 18157636.4.

\* cited by examiner

ULTRASONIC PROBE

CROSS-REFERENCE TO RELATED APPLICATION

This application claims the benefit of Korean Patent Application No. 10-2017-0022835, filed on Feb. 21, 2017 in the Korean Intellectual Property Office, the disclosure of which is incorporated herein by reference.

BACKGROUND

1. Field

Embodiments of the present disclosure relate to an ultrasonic probe apparatus which generates an image of the inside of a subject using ultrasonic waves, and more particularly, to a multi-row ultrasonic probe.

2. Description of the Related Art

An ultrasonic imaging apparatus is an apparatus which emits an ultrasonic signal toward a target area inside a body of a subject from a surface of the subject and noninvasively obtains a tomographic image of soft tissue of the subject or an image of a blood flow using information from an ultrasonic signal (an ultrasonic echo signal) reflected from the target part.

An ultrasonic imaging apparatus has a small size, is cheap, is capable of displaying an image in real time, causes no radiation exposure, and thus is very safe compared to other imaging diagnostic apparatuses such as an X-ray diagnostic apparatus, an X-ray computerized tomography (CT) scanner, a magnetic resonance imaging (MRI) apparatus, a nuclear medicine diagnostic apparatus, etc. Thus, ultrasonic imaging apparatuses have been widely used for diagnosis in the fields of cardiology, gastroenterology, urology, and obstetrics and gynecology.

The ultrasonic imaging apparatus may include an ultrasonic probe which transmits an ultrasonic signal to a subject and receives an ultrasonic echo signal reflected from the subject so as to obtain an ultrasonic image of the subject and a main body which generates an image of the inside of the subject using the ultrasonic echo signal received from the ultrasonic probe.

Existing single-row (1D) probes have a focal point physically fixed due to a lens curvature and are thus limited in terms of focal range.

Multi-row (1.25D to 1.75D) probes developed to address the problem of existing single-row (1D) probes are capable of physically or electrically adjusting a focal zone, thus forming a high-resolution image of a wider region. Accordingly, there is a recent trend of 1.25D (3 Row) or more multi-row probes replacing 1D (1 Row) probes.

A transducer is divided by dicing to manufacture a multi-row probe, but the transducer has a very small thickness margin and is very difficult to dice. Accordingly, dicing time increases, error rate is high, and failure costs are high.

SUMMARY

Therefore, it is an aspect of the present disclosure to provide a multi-row ultrasonic probe of which a manufacturing failure rate can be decreased through simple processing.

Additional aspects of the disclosure will be set forth in part in the description which follows and, in part, will be obvious from the description, or may be learned by practice of the disclosure.

In accordance with one aspect of the present disclosure, an ultrasonic probe includes a piezoelectric layer configured to generate ultrasonic waves; a sound layer provided on a rear side of the piezoelectric layer; a flexible printed circuit board provided on a rear side of the sound layer; and a sound absorption layer configured to absorb the ultrasonic waves generated by the piezoelectric layer and propagating toward a rear surface of the ultrasonic probe, the sound absorption layer being provided on a rear surface of the flexible printed circuit board. The piezoelectric layer includes a kerf configured to divide the piezoelectric layer in a direction of elevation. The sound layer includes a funnel extending in a direction extending from a front side of the sound layer to the rear side of the sound layer to divide the sound layer.

The funnel may include a first section connected to the piezoelectric layer; and a second section connected to the flexible printed circuit board. The first section and the second section may have different widths.

The first section may be provided at a location corresponding to the kerf to be connected to the kerf.

A width of the kerf may be the same as that of the first section.

The width of the first section may be less than that of the second section.

The width of the first section may be constant, and the width of the second section may change in the direction extending from the front side of the sound layer to the rear side of the sound layer.

The width of the first section and the width of the second section may be constant in the direction extending from the front side of the sound layer to the rear side of the sound layer.

The width of the first section may change in the direction extending from the front side of the sound layer to the rear side of the sound layer. The width of the second section may be constant. The width of the first section may be greater than that of the second section.

The sound layer may have higher acoustic impedance than that of the piezoelectric layer.

The sound layer may have electrical conductivity.

The sound layer may include at least one of tungsten carbide and a graphite composite material.

The sound layer may have a width which is ½, ¼, ⅛, or 1/16 of a wavelength of the piezoelectric layer.

The number of the kerfs may be two or more, and the number of funnels may be two or more.

In accordance with another aspect of the present disclosure, an ultrasonic probe includes a piezoelectric layer configured to generate ultrasonic waves, a flexible printed circuit board provided on a rear side of the piezoelectric layer; and a sound absorption layer configured to absorb the ultrasonic waves generated by the piezoelectric layer and propagating toward a rear surface of the ultrasonic probe, the sound absorption layer being provided on a rear surface of the flexible printed circuit board. The piezoelectric layer includes a funnel configured to divide the piezoelectric layer in a direction of elevation, the funnel having a section in which a width changes in a direction extending from a front side of the piezoelectric layer to the rear side of the piezoelectric layer.

The funnel may include a first section connected to the front side of the piezoelectric layer; and a second section connected to the flexible printed circuit board. The first section and the second section may have different widths.

The width of the first section may be less than that of the second section.

The width of the first section may be constant, and the width of the second section may change in a direction extending from a front side of the piezoelectric layer to a rear side of the piezoelectric layer.

The width of the first section and the width of the second section may be constant in a direction extending from a front side of the piezoelectric layer to a rear side of the piezoelectric layer.

The number of the funnels may be two or more funnels.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
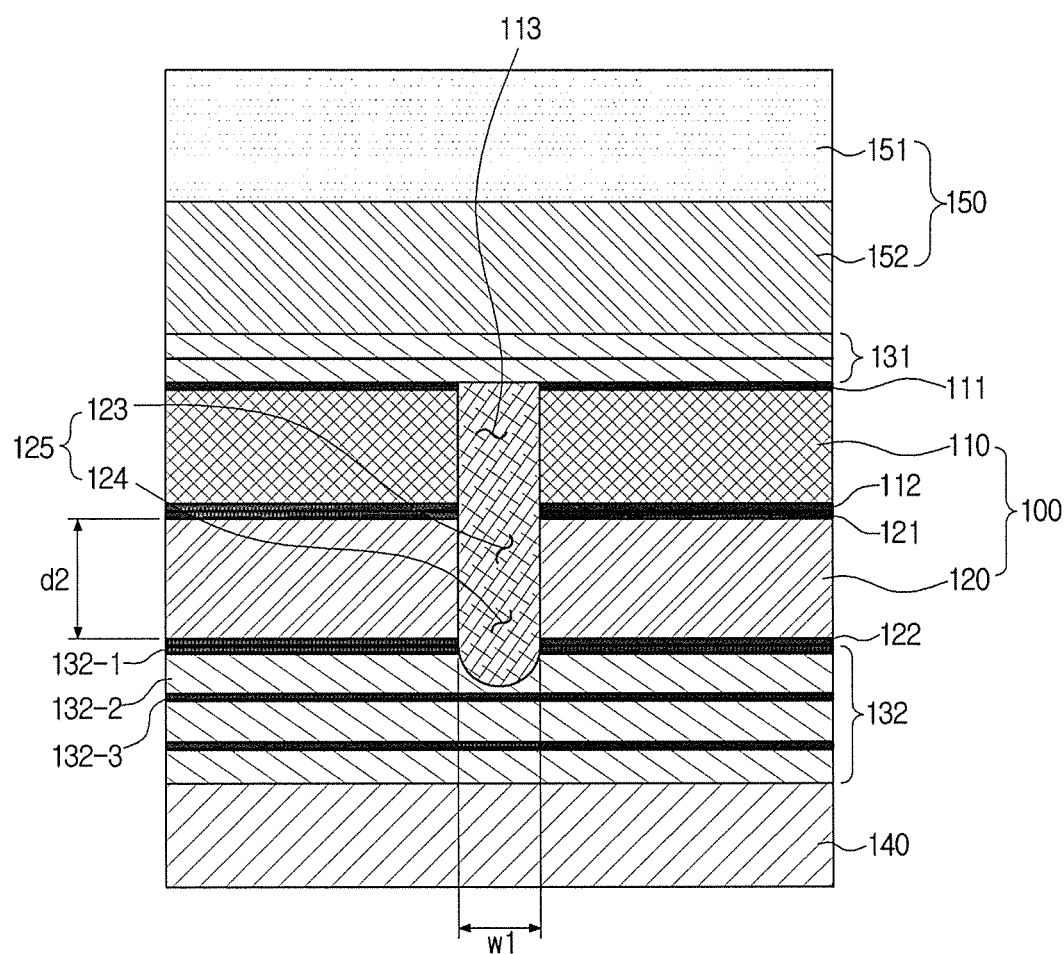
FIG. 1 is a cross-sectional view of a structure of a conventional ultrasonic probe.

Reference will now be made in detail to the embodiments of the present disclosure, examples of which are illustrated in the accompanying drawings, wherein like reference numerals refer to like elements throughout.

Hereinafter, ultrasonic probes in accordance with embodiments of the present disclosure will be described in detail with reference to the accompanying drawings.

Figure 2:
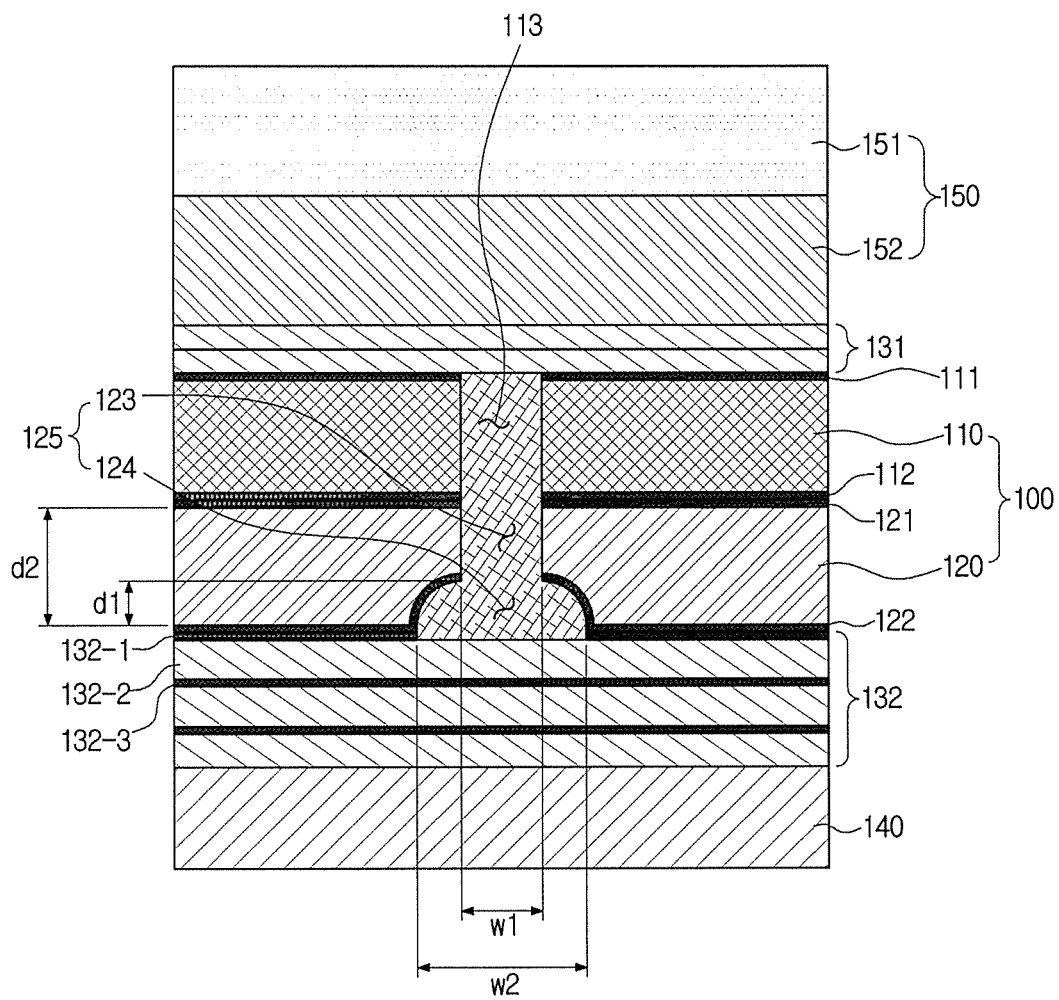
FIG. 2 is a cross-sectional view of an ultrasonic probe in accordance with an embodiment of the present disclosure.

FIG. 2 is a cross-sectional view of an ultrasonic probe in accordance with an embodiment of the present disclosure.

Referring to FIG. 2, the ultrasonic probe in accordance with an embodiment of the present disclosure includes a transducer layer 100, a matching layer 150 provided on a front side of the transducer layer 100, a sound absorption layer 140 provided on a rear side of the transducer layer 100, and a signal electrode 132 provided between the transducer layer 100 and the sound absorption layer 140.

In one embodiment, a magnetostrictive ultrasonic transducer using a magnetostrictive effect of a magnetic substance, a capacitive micromachined ultrasonic transducer transmitting or receiving ultrasonic waves using the vibration of several hundreds or several thousands of micromachined thin films, or a piezoelectric ultrasonic transducer using a piezoelectric effect of a piezoelectric material may be used as a transducer. Hereinafter, the piezoelectric ultrasonic transducer will be described as an embodiment of a transducer.

Effects of a voltage being generated when mechanical pressure is applied to a certain material and a material being mechanically deformed when a voltage is applied thereto are respectively referred to as the piezoelectric effect and an inverse piezoelectric effect. A material having the effects is referred to as a piezoelectric material.

That is, the piezoelectric material is a material that converts electric energy into mechanical vibration energy and converts mechanical vibration energy into electric energy.

The transducer layer 100 in accordance with an embodiment of the present disclosure includes a piezoelectric layer 110 formed of a piezoelectric material which generates ultrasonic waves by converting an electrical signal applied thereto into mechanical vibration, and a sound layer 120 provided on a rear side of the piezoelectric layer 110.

Examples of the piezoelectric material of the piezoelectric layer 110 may include ceramic of lead zirconate titanate (PZT), PZMT single crystal formed of a solid solution of lead magnesium niobate and lead titanate, PZNT single crystal formed of a solid solution of lead zinc niobate and lead titanate, etc.

The sound layer 120 may have higher acoustic impedance than that of the piezoelectric layer 110. The sound layer 120 may be formed of a material having electrical conductivity. A thickness of the sound layer 120 may be ½, ¼, ⅛, or 1/16 of a wavelength of the piezoelectric material of the piezoelectric layer 110. That is, when the wavelength of the piezoelectric material of the piezoelectric layer 110 is λ, the thickness of the sound layer 120 may be ½λ, ¼λ, ⅛λ or 1/16λ.

In an embodiment of the present disclosure, the sound layer 120 may be an acoustic reflector. The acoustic reflector may be provided in front of the sound absorption layer 140. The acoustic reflector may completely reflect ultrasonic waves propagating toward the sound absorption layer 140. A bandwidth and sensitivity of the ultrasonic probe may be increased using the acoustic reflector.

The acoustic reflector may be formed of a material having very high acoustic impedance to completely reflect ultrasonic waves. For example, the sound layer 120 may be formed of a material having very high acoustic impedance. For example, the sound layer 120 may be formed of at least one of tungsten carbide and a graphite composite material.

An electrode to which an electrical signal may be supplied may be formed on the front and rear surfaces of the transducer layer 100. A ground electrode 131 may be formed on the front surface of the transducer layer 100. A signal electrode 132 may be formed on the rear surface of the transducer layer 100. Each of the ground electrode 131 and the signal electrode 132 may be a flexible printed circuit board.

As shown in FIG. 2, electrodes may be formed a front surface and a rear surface of the piezoelectric layer 110. For example, a first electrode 111 connected to the ground electrode 131 may be provided on the front surface of the piezoelectric layer 110, and a second electrode 112 electrically connected the signal electrode 132 may be provided on the rear surface of the piezoelectric layer 110. Alternatively, the first electrode 111 formed on the front surface of the piezoelectric layer 110 may be connected to the signal electrode 132, and the second electrode 112 formed on the rear surface of the piezoelectric layer 110. Alternatively, the first electrode 111 formed on the front surface of the piezoelectric layer 110 may be connected to the signal electrode 132, and the second electrode 112 formed on the rear surface of the piezoelectric layer 110 may be connected to the ground electrode 131.

The sound layer 120 may include a third electrode 121 and a fourth electrode 122. The third electrode 121 may be formed on a front surface of the sound layer 120, and the fourth electrode 122 may be formed on a rear surface of the sound layer 120. The third electrode 121 and the fourth electrode 122 may be electrically connected. That is, the third electrode 121 and the fourth electrode 122 may be short-circuited. The third electrode 121 and the fourth electrode 122 are illustrated in FIG. 2, but the present disclosure is not limited thereto. Unlike shown in the drawings, the sound layer 120 may not include the electrodes formed on the front and rear surfaces thereof. In this case, the sound layer 120 may be formed of a conductive material. When the sound layer 120 is formed of the conductive material, the sound layer 120 may be electrically connected to the second electrode 112 and the signal electrode 132 without the third electrode 121 and the fourth electrode 122.

The matching layer 150 is provided on the front surface of the transducer layer 100. The matching layer 150 matches acoustic impedances of the transducer layer 100 and a subject by decreasing an impedance difference between the transducer layer 100 and the subject so that ultrasonic waves generated by the transducer layer 100 may be efficiently transmitted to the subject.

To this end, the impedance of the matching layer 150 may have a median value between the acoustic impedance of the transducer layer 100 and the acoustic impedance of the subject. In detail, the impedance of the matching layer 150 may have a median value between an acoustic impedance of the piezoelectric layer 110 and the acoustic impedance of the subject.

The matching layer 150 may include a plurality of matching layers to change acoustic impedance stepwise from the transducer layer 100 toward the subject. As illustrated in FIG. 2, the matching layer 150 may include a first matching layer 151 and a second matching layer 152. The plurality of matching layers 150 may be formed of different materials. The matching layer 150 may be formed of glass or a resin material.

Although not shown, a lens may be provided on a front surface of the matching layer 150. The lens may focus ultrasonic waves generated by the piezoelectric layer 110. The lens may be formed of a material, such as silicon or rubber, having substantially the same acoustic impedance as that of the subject. The lens may be a convex type lens of which a central part has a convex curved surface or may be a linear type lens having a flat surface.

The sound absorption layer 140 may be provided on the rear side of the transducer layer 100. The sound absorption layer 140 may prevent distortion of an ultrasonic image by suppressing free vibration of the piezoelectric layer 110 to decrease a pulse width of ultrasonic waves and preventing the ultrasonic waves from unnecessarily propagating behind the piezoelectric layer 110. The sound absorption layer 140 may be formed of a material containing rubber to which epoxy resin, tungsten power, etc. are added.

According to an embodiment of the present disclosure, the ultrasonic probe may be a multi-row probe.

A single-row (1D) probe includes a plurality of elements as the transducer layer 100 is divided in an azimuth direction. Here, the transducer layer 100 is not divided in a direction of elevation. The single-row probe has a physical focal zone due to lens curvature, and thus the focal zone is fixed. Accordingly, the single-row probe is limited in terms of the focal zone.

In multi-row (1.25D to 1.75D) probes, the transducer layer 100 is divided in the direction of elevation, as well as the azimuth direction. In detail, an element of a 1.25D probe is divided into three parts in the direction of elevation, an element of a 1.5D probe is divided into four parts in the direction of elevation, and an element of a 1.75D probe is divided into five parts in the direction of elevation. That is, the multi-row probes include elements arranged in three to five rows in the direction of elevation.

In such multi-row probes, a focusing region may be physically and electrically adjusted, and thus a high-resolution image of a wider region may be obtained.

FIG. 1 is a cross-sectional view of a structure of a conventional ultrasonic probe.

In order to manufacture the multi-row probe, the transducer layer 100 is divided by dicing in the direction of elevation. In accordance with the present embodiment, the transducer layer 100 includes the piezoelectric layer 110 and the sound layer 120, and thus the piezoelectric layer 110 and the sound layer 120 should be divided by dicing in the direction of elevation.

As shown in FIG. 1, the signal electrode 132 provided on the rear surface of the sound layer 120 may include a fifth electrode 132-1, a polyimide film 132-2, and a sixth electrode 132-3.

Conventionally, in order to manufacture the multi-row probe, some of the fifth electrode 132-1 and the polyimide film 132-2 are divided by dicing. In this case, a dicing thickness margin may be a thickness of the polyimide film 132-2. The multi-row may be formed by dividing the fifth electrode 132-1, whereas the wiring pattern of the signal electrode 132 is disconnected when the sixth electrode 132-3 is divided.

The polyimide film 132-2 may have a thickness of about 12 μm. In this case, a thickness margin when the transducer layer 100 is divided in the direction of elevation may be 12 μm, corresponding to a thickness of the polyimide film 132-2. That is, a thickness margin between the transducer layer 100 and the signal electrode 132 is very small. Therefore, the sound layer 120 was not divided when a cutting depth of the dicing was extremely small, and a wiring pattern of the signal electrode 132 was disconnected to cause a defect when the cutting depth was extremely large. Conventionally, as described above, since a cutting thickness margin of the dicing was extremely small, an error rate was high during manufacture of the multi-row probe. Furthermore, an intermediate process inspection could not be performed, and thus failure costs were also high.

According to an embodiment of the present disclosure, a process error rate of the multi-row probe may be decreased by simple processing of the transducer layer 100. To this end, the piezoelectric layer 110 in accordance with an embodiment of the present disclosure may include a kerf 113 and the sound layer 120 may include a funnel 125.

The piezoelectric layer 110 may include the kerf 113 configured to divide the piezoelectric layer 110 in the direction of elevation. The kerf 113 may be formed using a dicing process. Although only one kerf 113 is illustrated in the drawings, two or more kerfs 113 may be formed to be spaced apart from each other in the direction of elevation. In order to manufacture a 1.25D probe, two kerfs 113 may be formed. In order to manufacture a 1.5D probe, three kerfs 113 may be formed. In order to manufacture a 1.75D probe, four kerfs 113 may be formed.

The sound layer 120 may include the funnel 125. The funnel 125 may be provided to be connected to the kerf 113 formed on the piezoelectric layer 110. The funnel 125 may be provided to divide the sound layer 120 in the direction of elevation.

The funnel 125 may include a first section 123 connected to the kerf 113 and a second section 124 connected to the signal electrode 132.

The first section 123 may be formed at a location corresponding to the kerf 113 in order to be connected to the kerf 113. A width of the first section 123 may be the same as that of the kerf 113 since the first section 123 and the kerf 113 are formed together using the dicing process.

The second section 124 may be concave toward the inside of the sound layer 120. The second section 124 may be formed on the sound layer 120 before the first section 123 is formed. That is, the second section 124 may be formed on the sound layer 120 by preprocessing. The second section 124 is formed only on the sound layer 120, and is not formed on the flexible printed circuit board (namely, signal electrode) 132. Similar to the kerf 113, two second sections 124 may be previously formed in the case of a 1.25D probe. Three second sections 124 may be previously formed in the case of a 1.5D probe. Four second sections 124 may be previously formed in the case of al 0.75D probe.

The funnel 125 may be provided by forming the first section 123 on the preprocessed second section 124 using the dicing process. As will be described below, the second section 124 is provided to secure a cutting margin when an element is divided. Thus, the second section 124 is formed only on the sound layer 120 and is not formed on the flexible printed circuit board 132.

The first section 123 and the kerf 113 may be formed together using the dicing process.

The second section 124 may decrease an error rate during manufacture of the multi-row probe. In detail, the second section 124 may increase a thickness margin when an element is divided. With the second section 124, a cutting margin may be secured when an element is divided. As previously described, an element cannot be divided when a cutting depth is extremely small, and the signal electrode 132 may be inadvertently cut and an error may occur when the cutting depth is extremely large. When the second section 124 is formed in advance on the sound layer 120, a thickness margin corresponding to a depth d1 of the second section 124 may be secured. As the thickness margin increases, a cutting error rate may decrease. When the cutting error decreases, failure costs may decrease.

As illustrated in FIG. 2, a width w1 of the first section 123 may be less than a width w2 of the second section 124. The width w1 of the first section may be equal to a dicing thickness. When the width w2 of the second section is greater than the dicing thickness equal to the width w1, a thickness margin may be secured in the azimuth direction during the dicing process.

The depth d1 of the second section 124 may be less than a thickness d2 of the sound layer 120. The kerf 113 may be provided to have a constant width in a direction extending from the front side of the piezoelectric layer 110 to the rear side thereof. Similarly, the first section 123 may be provided to have a constant width in a direction extending from the front side of the sound layer 120 to the rear side thereof.

The second section 124 may be provided such that a width thereof changes in the direction extending from the front side of the sound layer 120 to the rear side thereof. In detail, the width of the second section 124 may increase as the distance between the second section 124 and the signal electrode 132 decreases. The second section 124 may have a semicircular cross section. Furthermore, the depth d1 of the second section 124 at a point at which the second section 124 and the first section 123 meet each other may be a maximum depth of the second section 124.

As shown in FIG. 2, the first electrode 132-1 of the signal electrode 132 may be divided by pre-processing. The pre-processing may include various methods. For example, when a flexible printed circuit board is formed, a region therein corresponding to the funnel 125 may be formed without the first electrode 132-1.

According to the embodiment of the present disclosure, in order to manufacture the multi-row probe, a process in which the fifth electrode 132-1 is divided by dicing may be omitted. As described above, in the case in which the sixth electrode 132-3 is not divided and only the fifth electrode 132-1 is divided, a failure rate is high and failure costs are also high. According to the embodiment of the present disclosure, the failure rate in the manufacturing process of the multi-row probe may be decreased due to the omission of the above process.

Figure 3:
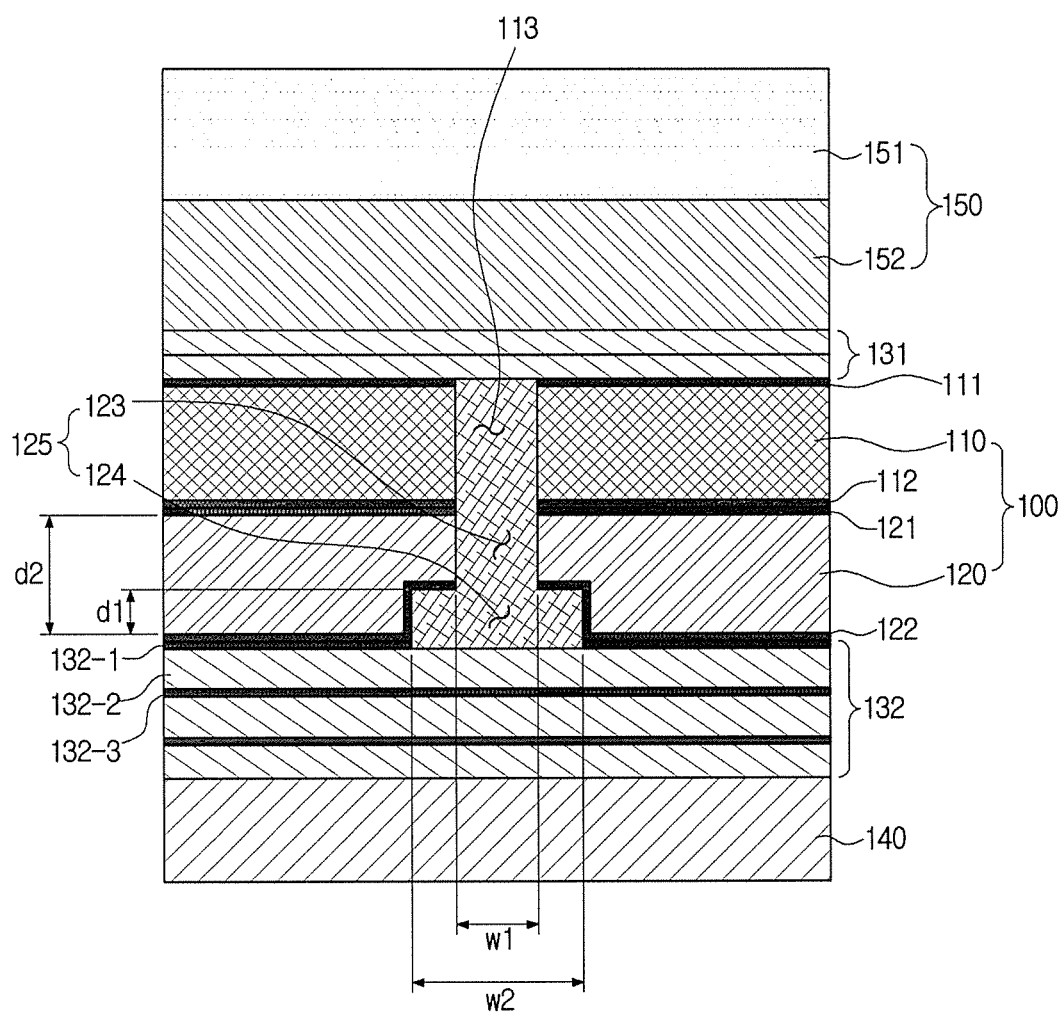
FIG. 3 is a cross-sectional view of an ultrasonic probe in accordance with another embodiment of the present disclosure.

FIG. 3 is a cross-sectional view of an ultrasonic probe in accordance with another embodiment of the present disclosure. A description of parts of the ultrasonic probe illustrated in FIG. 3 which are the same as those in prior description will be omitted here.

In the embodiment of FIG. 3, a funnel 125 may have a structure different from that in the embodiment of FIG. 2. More specifically, a width w2 of a second section 124 of the funnel 125 may be constant in a direction extending from a front side of a sound layer 120 to a rear side thereof. The second section 124 may have a rectangular cross section.

Figure 4:
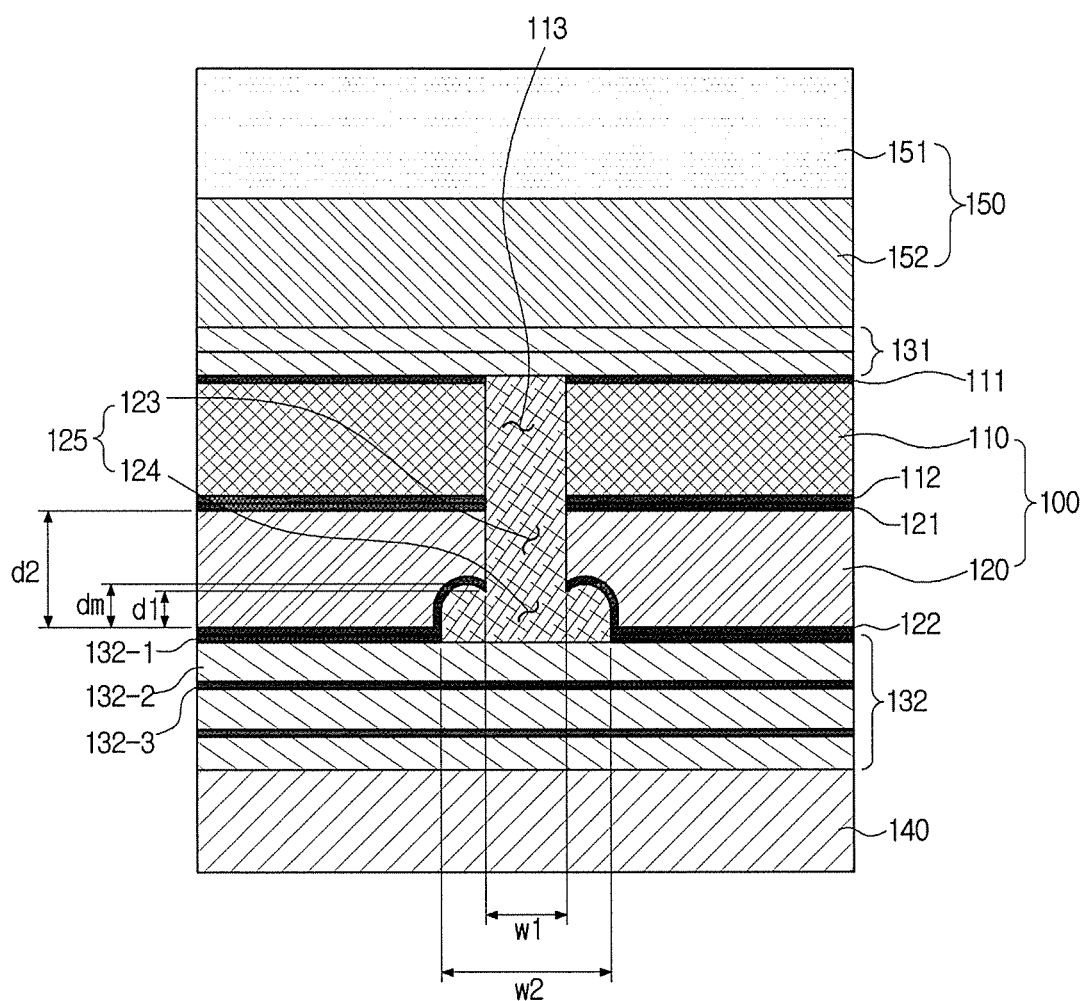
FIG. 4 is a cross-sectional view of an ultrasonic probe in accordance with another embodiment of the present disclosure.

FIG. 4 is a cross-sectional view of an ultrasonic probe in accordance with another embodiment of the present disclosure. A description of parts of the ultrasonic probe illustrated in FIG. 4 which are the same as those in the above description will be omitted here.

In the embodiment of FIG. 4, a funnel 125 may have a structure different from those in the embodiments of FIGS. 2 and 3. In the present embodiment, a depth d at a point at which a second section 124 and a first section 123 of the funnel 125 meet each other may be different from a maximum depth dm of the second section 124.

Figure 5:
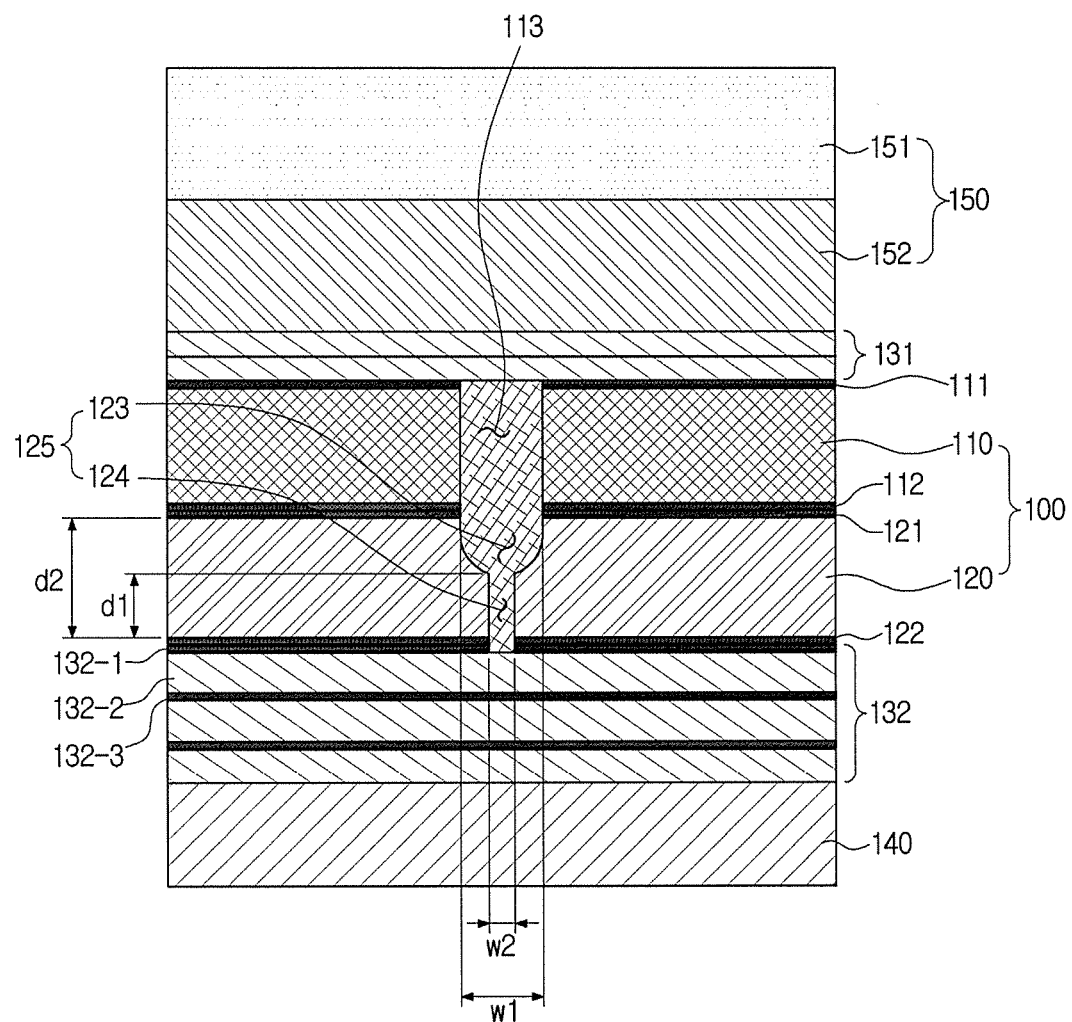
FIG. 5 is a cross-sectional view of an ultrasonic probe in accordance with another embodiment of the present disclosure.

FIG. 5 is a cross-sectional view of an ultrasonic probe in accordance with another embodiment of the present disclosure. A description of parts of the ultrasonic probe illustrated in FIG. 5 which are the same as those in the above description will be omitted here.

In the embodiment of FIG. 5, a funnel 125 may have a structure different from those in the embodiments of FIGS. 2 to 4. In the present embodiment, a width w2 of a second section of the funnel 125 may be less than a width w1 of a first section thereof. The width w2 of the second section may be constant in a direction extending from a front side of a sound layer 120 to a rear side thereof. A width of the first section 123 may change in the direction extending from the front side of the sound layer 120 to the rear side thereof.

Although FIGS. 2 to 5 illustrate that the funnel 125 has bilateral symmetry, embodiments are not limited thereto. The funnel 125 may have bilateral asymmetry due to an error during a manufacturing process.

Figure 6:
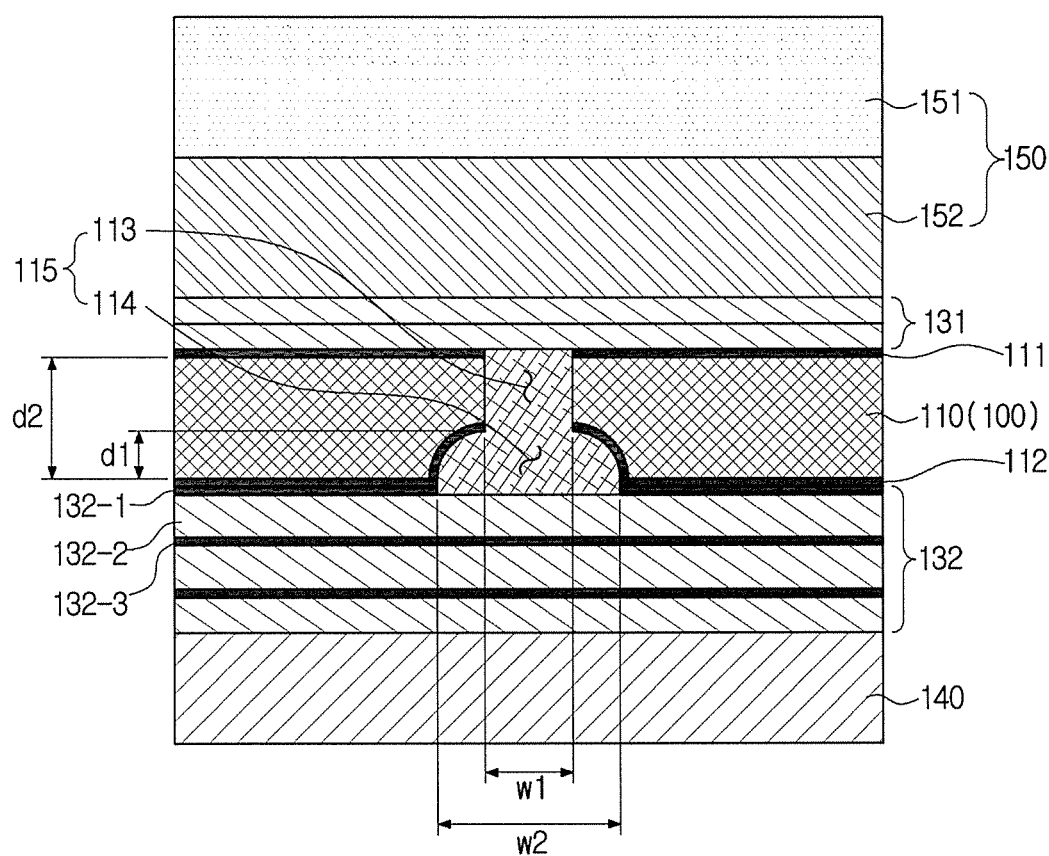
FIG. 6 is a cross-sectional view of an ultrasonic probe in accordance with another embodiment of the present disclosure.

FIG. 6 is a cross-sectional view of an ultrasonic probe in accordance with another embodiment of the present disclosure. In the embodiment of FIG. 6, a transducer layer 100 of the ultrasonic probe may include only a piezoelectric layer 110. That is, in the embodiment of FIG. 6, the transducer layer 100 does not include a sound layer.

In the embodiment of FIG. 6, a funnel 115 may be formed on the piezoelectric layer 110. The funnel 115 may include a first section 113 and a second section 114, similar to those in the embodiments of FIGS. 2 to 5.

A width w1 of the first section 113 may be less than a width w2 of the second section 114. The width w1 of the first section 113 may be constant in a direction extending from a front side of the piezoelectric layer 110 to a rear side thereof. The width w2 of the second section 114 may change in the direction extending from the front side of the piezoelectric layer 110 to the rear side thereof.

The second section 114 may have a maximum depth d1 at a point at which the first section 113 and the second section 114 meet each other. A depth of the second section 114 may decrease toward an outer side of the funnel 115.

Figure 7:
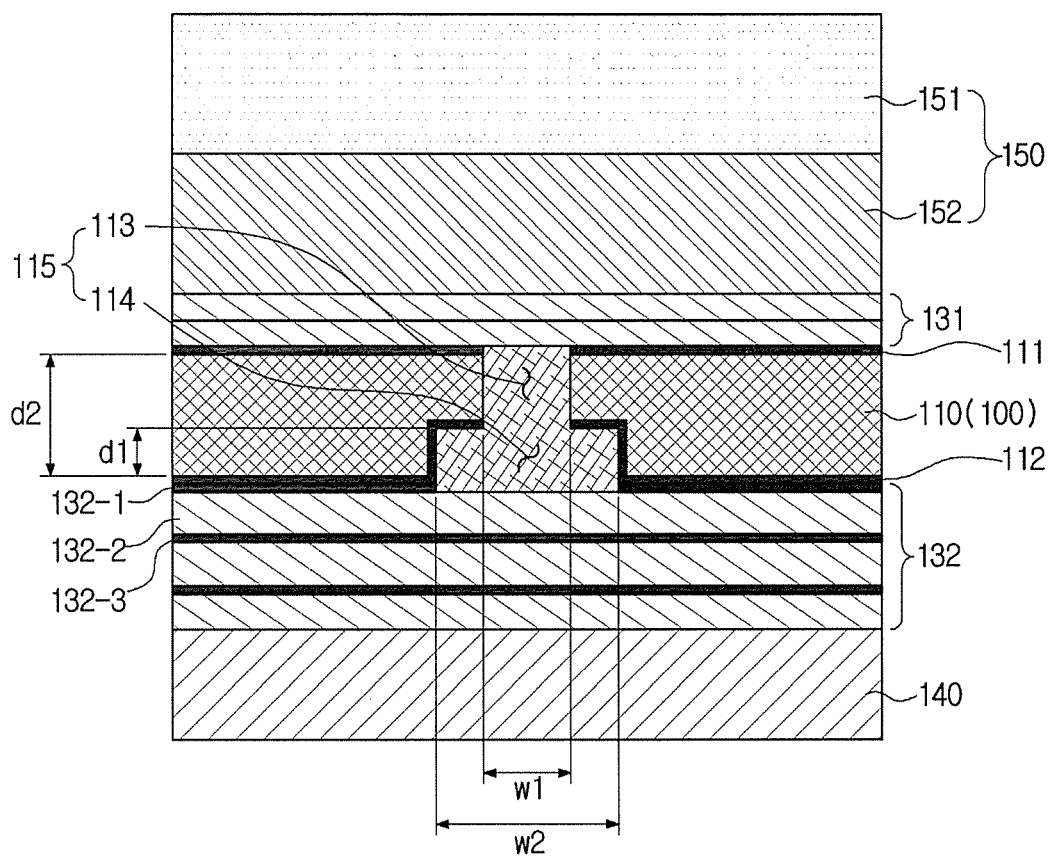
FIG. 7 is a cross-sectional view of an ultrasonic probe in accordance with another embodiment of the present disclosure.

FIG. 7 is a cross-sectional view of an ultrasonic probe in accordance with another embodiment of the present disclosure. In the embodiment of FIG. 7, a sound layer is not provided as in the embodiment of FIG. 6. Furthermore, a funnel 115 may be formed on a piezoelectric layer 110.

In the embodiment of FIG. 7, a width w1 of a first section 113 of the funnel 115 may be less than a width w2 of a second section 114 thereof. The width w1 of the first section 113 and the width w2 of the second section 114 may each be constant in a direction extending from a front side of the piezoelectric layer 110 to a rear side thereof. In the present embodiment, a depth d1 of the second section 114 may be constant.

Figure 8:
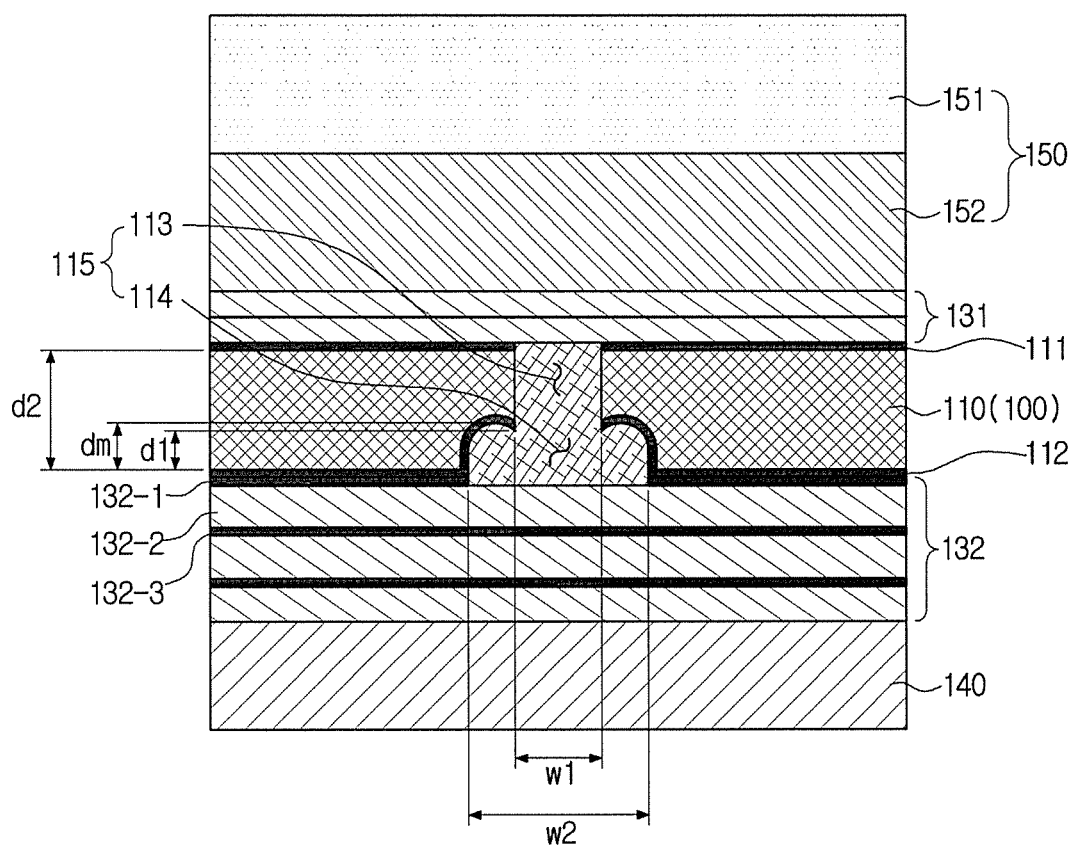
FIG. 8 is a cross-sectional view of an ultrasonic probe in accordance with another embodiment of the present disclosure.

FIG. 8 is a cross-sectional view of an ultrasonic probe in accordance with another embodiment of the present disclosure. In the embodiment of FIG. 8, a sound layer is not provided as in the embodiments of FIGS. 6 and 7. A funnel 115 may be formed on a piezoelectric layer 110.

In the embodiment of FIG. 8, a width w1 of a first section 113 of the funnel 115 may be less than a width w2 of a second section 114 thereof.

The width w1 of the first section 113 may be constant in a direction extending from a front side of the piezoelectric layer 110 to a rear side thereof. In contrast, the width w2 of the second section 114 may change in the direction extending from the front side of the piezoelectric layer 110 to the rear side thereof.

The second section 114 may not have a maximum depth dm at a point at which the first section 113 and the second section 114 meet each other. A depth d1 at the point at which the first section 113 and the second section 114 meet each other may be different from the maximum depth dm of the second section 114. A depth of the second section 114 may not be constant.

Figure 9:
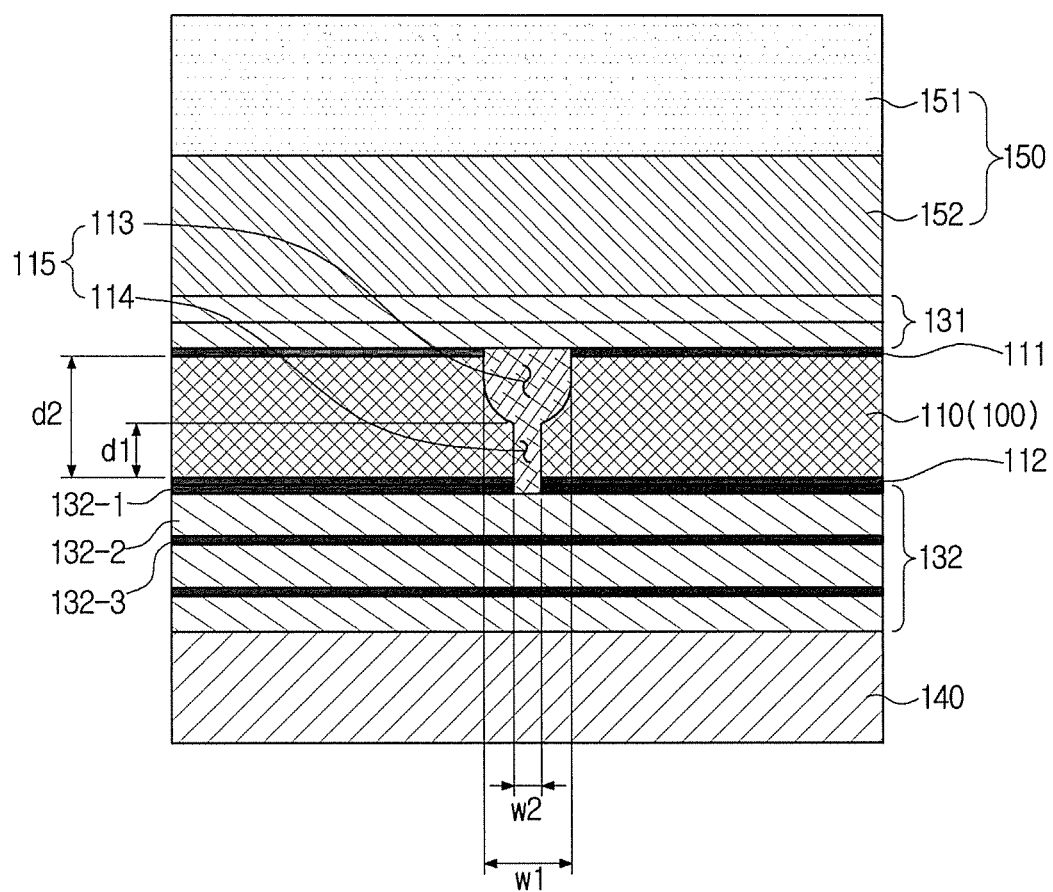
FIG. 9 is a cross-sectional view of an ultrasonic probe in accordance with another embodiment of the present disclosure.

FIG. 9 is a cross-sectional view of an ultrasonic probe in accordance with another embodiment of the present disclosure. In the embodiment of FIG. 9, a sound layer is not provided as in the embodiments of FIGS. 6 to 8. A funnel 115 may be formed on a piezoelectric layer 110.

The funnel 115 may include a first section 113 and a second section 114. In the present embodiment, a width w2 of the second section 114 may be less than a width w1 of the first section 113. The width w1 of the first section 113 may change in a direction extending from a front side of the piezoelectric layer 110 to a rear side thereof. The width w1 of the first section 113 may decrease from the front side of the piezoelectric layer 110 to the rear side thereof. The width w2 of the second section 114 may be constant in the direction extending from the front side of the piezoelectric layer 110 to the rear side thereof.

Although the funnel 115 is illustrated as having bilateral symmetry in FIGS. 6 to 9, embodiments are not limited thereto. The funnel 115 may have bilateral asymmetry due to an error during a manufacturing process.

As is apparent from the above description, according to the present disclosure, a multi-row ultrasonic probe of which a manufacturing failure rate can be decreased through simple processing is provided.

Modifications or changes can be made in the present disclosure within an equivalent range and/or within a range of technical field or knowledge of the present disclosure. The embodiments set forth herein are merely intended to describe best modes for implementing a technical idea of the present disclosure, and various changes can be made as required in fields and purposes to which the present disclosure is applicable. Accordingly, the embodiments set forth in the above detailed description of the present disclosure should not be construed as limiting the scope of the present disclosure. Furthermore, the appended claims should be understood to include other various embodiments.

What is claimed is:

1. An ultrasonic probe comprising:
   a piezoelectric layer configured to generate ultrasonic waves;
   a sound layer provided on a rear side of the piezoelectric layer;
   a flexible printed circuit board provided on a rear side of the sound layer; and
   a sound absorption layer configured to absorb the ultrasonic waves generated by the piezoelectric layer and propagating toward a rear surface of the ultrasonic probe, the sound absorption layer being provided on a rear surface of the flexible printed circuit board,
   wherein the piezoelectric layer comprises a kerf configured to divide the piezoelectric layer in a direction of elevation,
   the sound layer comprises a funnel extending in a direction extending from a front side of the sound layer to the rear side of the sound layer to divide the sound layer,
   the flexible printed circuit board includes a plurality of divided first electrodes, a second electrode, and a polyimide film disposed between the plurality of divided first electrodes and the second electrode, and
   a distance between the plurality of divided first electrodes is equal to a maximum width of the funnel.

2. The ultrasonic probe according to claim 1, wherein the funnel comprises:
   a first section connected to the piezoelectric layer; and
   a second section connected to the flexible printed circuit board,
   wherein the first section and the second section have different widths.

3. The ultrasonic probe according to claim 2, wherein the first section is provided at a location corresponding to the kerf to be connected to the kerf.

4. The ultrasonic probe according to claim 3, wherein a width of the kerf is the same as that of the first section.

5. The ultrasonic probe according to claim 2, wherein the width of the first section is less than that of the second section.

6. The ultrasonic probe according to claim 5, wherein the width of the first section is constant, and the width of the second section changes in the direction extending from the front side of the sound layer to the rear side of the sound layer.

7. The ultrasonic probe according to claim 5, wherein the width of the first section and the width of the second section are constant in the direction extending from the front side of the sound layer to the rear side of the sound layer.

8. The ultrasonic probe according to claim 2, wherein the width of the first section changes in the direction extending from the front side of the sound layer to the rear side of the sound layer, the width of the second section is constant, and the width of the first section is greater than that of the second section.

9. The ultrasonic probe according to claim 1, wherein the sound layer has higher acoustic impedance than that of the piezoelectric layer.

10. The ultrasonic probe according to claim 1, wherein the sound layer has electrical conductivity.

11. The ultrasonic probe according to claim 1, wherein the sound layer comprises at least one of tungsten carbide and a graphite composite material.

12. The ultrasonic probe according to claim 1, wherein the sound layer has a width which is ½, ¼, ⅛, or 1/16 of a wavelength of the piezoelectric layer.

13. The ultrasonic probe according to claim 1, wherein the number of the kerfs is two or more, and the number of the funnels is two or more.

* * * * *